United States Patent [19]

Hunter et al.

[11] 4,353,367

[45] Oct. 12, 1982

[54] CONTAINER FOR STERILIZING A FLEXIBLE TUBE

[75] Inventors: Elisa Hunter, Cypress; Susan Gandy, Houston, both of Tex.

[73] Assignee: The Clinipad Corporation, Guilford, Conn.

[21] Appl. No.: 206,851

[22] Filed: Nov. 14, 1980

[51] Int. Cl.³ .............................................. A61M 5/00
[52] U.S. Cl. ................................ 128/213 A; 128/247; 422/300
[58] Field of Search ..................... 128/1 R, 247, 214.2, 128/213 A, 334 C, DIG. 26; 422/300

[56] References Cited

U.S. PATENT DOCUMENTS

| | | |
|---|---|---|
| 1,343,779 | 6/1920 | Herbert . |
| 1,940,763 | 12/1933 | Mays ................................. 422/300 |
| 2,831,487 | 4/1958 | Tafilaw ....................... 128/DIG. 26 |
| 3,013,656 | 12/1961 | Murphy ......................... 422/300 X |
| 3,488,141 | 1/1970 | Rausing .............................. 422/300 |
| 3,986,508 | 10/1976 | Barrington ...................... 128/214.2 |
| 4,141,956 | 2/1979 | Lemchen ............................ 422/116 |
| 4,209,013 | 6/1980 | Alexander et al. ............. 128/213 A |
| 4,306,976 | 12/1981 | Bazzato .......................... 128/213 A |

Primary Examiner—Dalton L. Truluck
Attorney, Agent, or Firm—St. Onge, Steward, Johnston & Reens

[57] ABSTRACT

A lightweight disposable container is described for in situ sterilization of a portion of a flexible tube such as the exposed end of a permanently embedded peritoneal catheter. The container has a basin and means for retaining the catheter portion to be sterilized in the vicinity of the basin bottom for submergence in a sterilizing solution in the basin. In one embodiment, a plurality of projections which are an integrally molded part of the container are spaced from each other at inlets to frictionally clamp the catheter in a gap formed between the projections. In another embodiment, the projections are formed in a hinged lid so that when the lid is closed the catheter or other tubing used in the procedure may be retained submerged under the solution. Several forms and locations for projections are disclosed.

23 Claims, 20 Drawing Figures

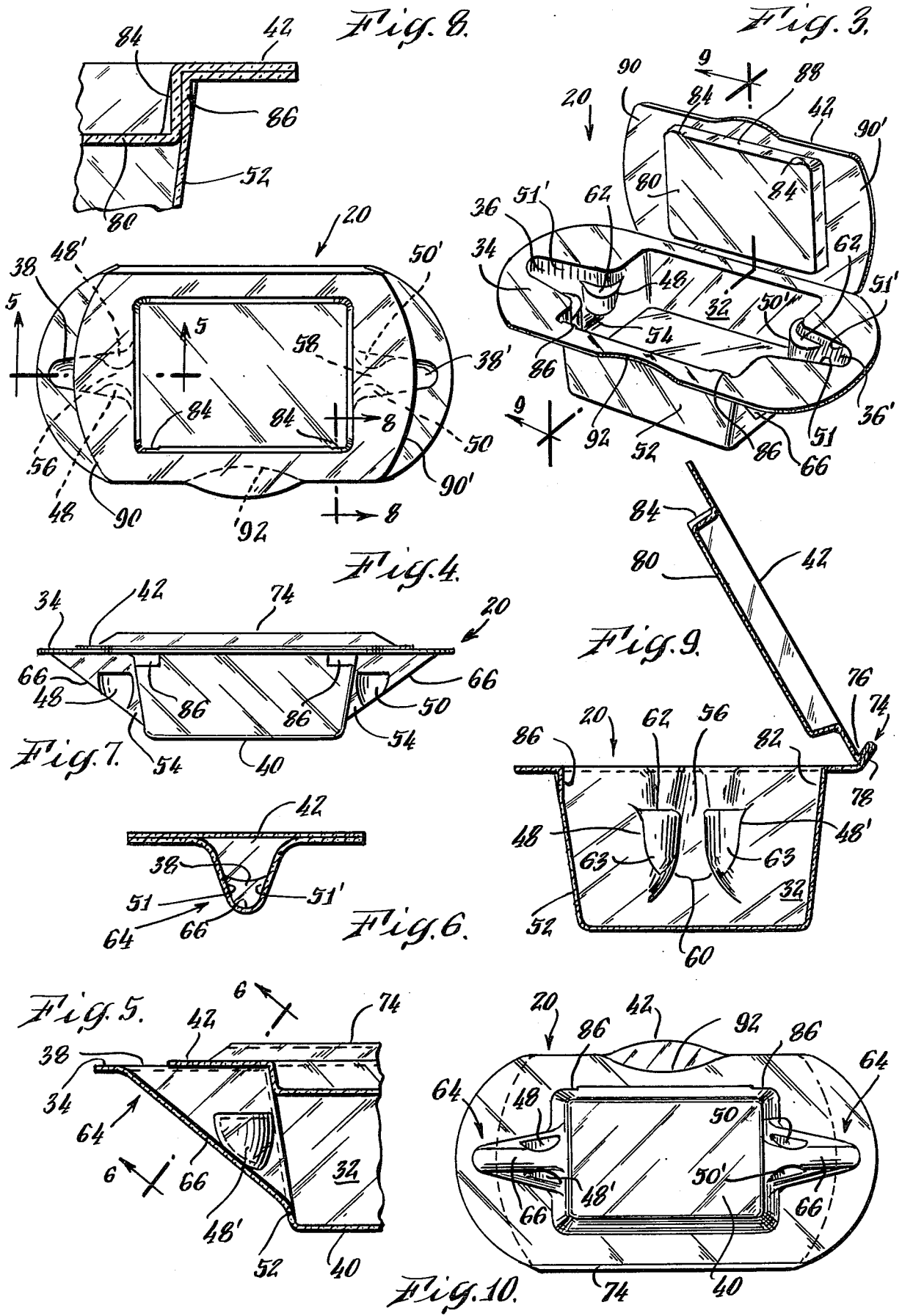

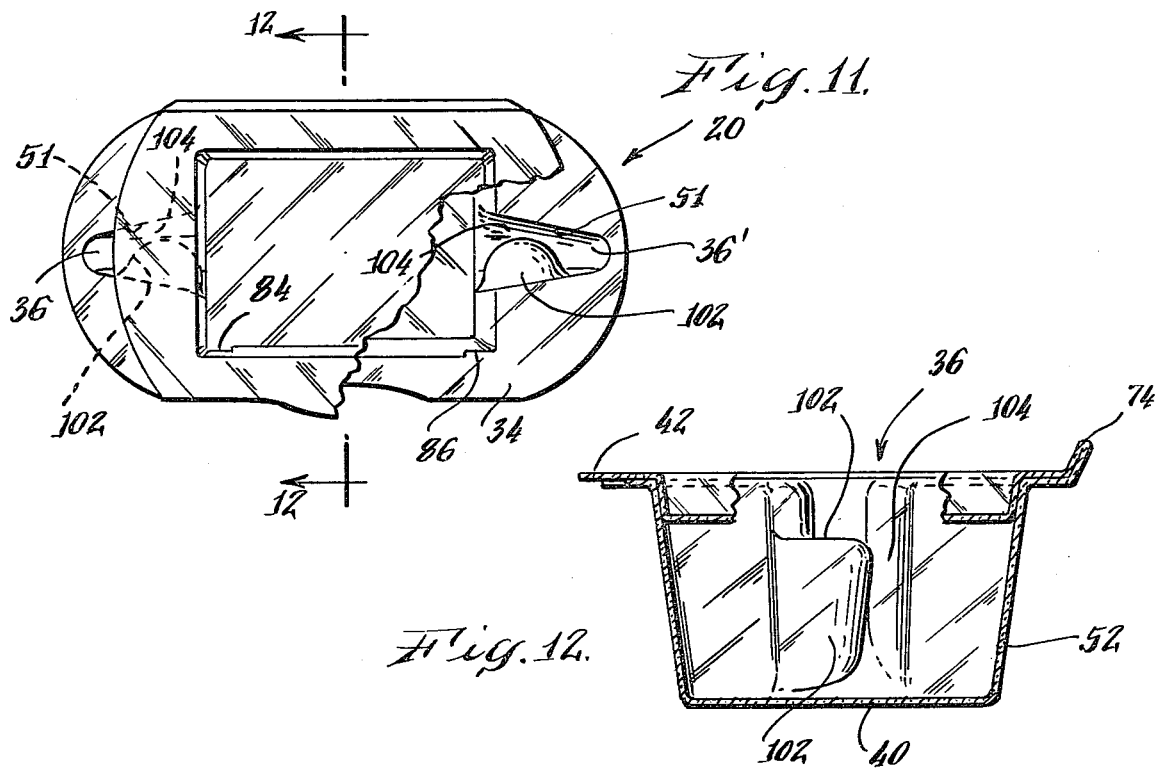
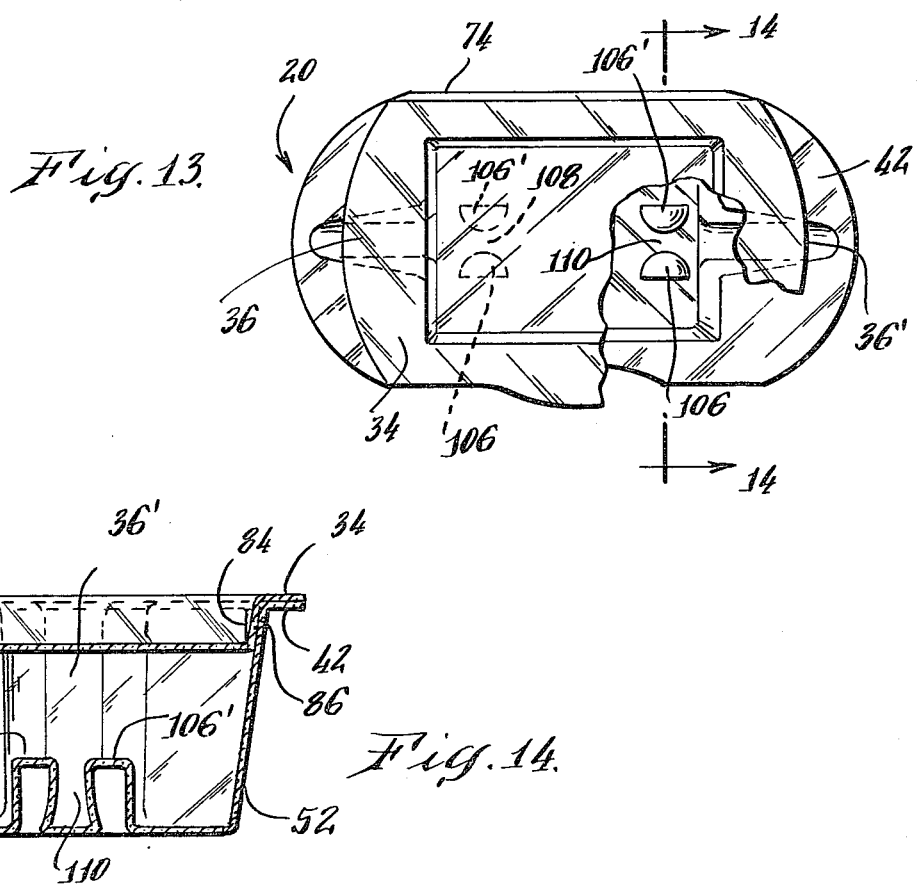

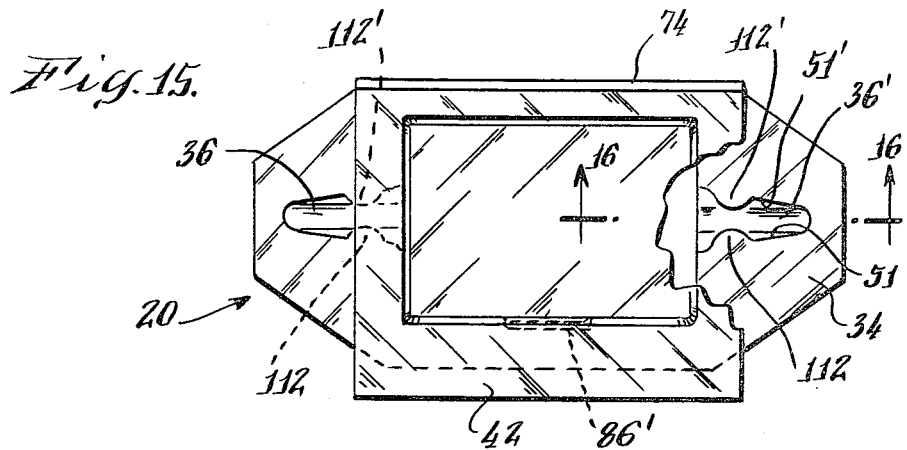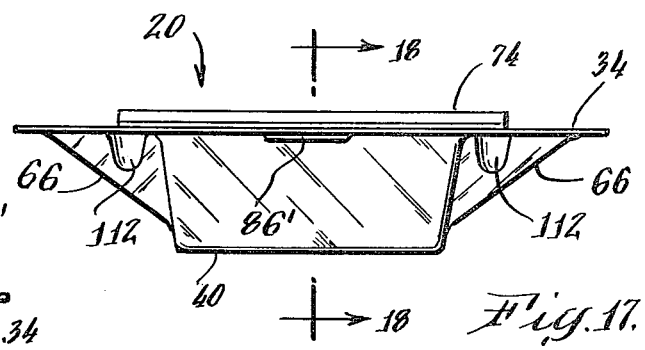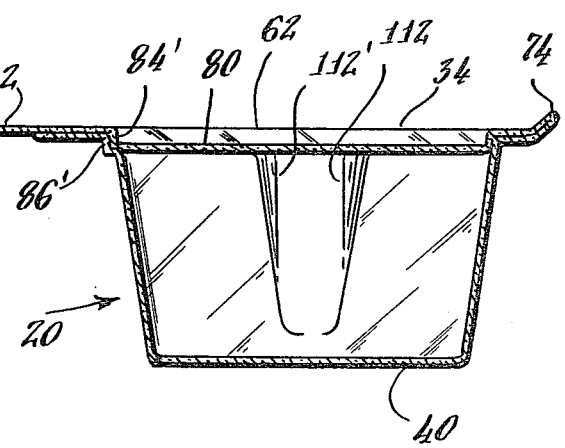

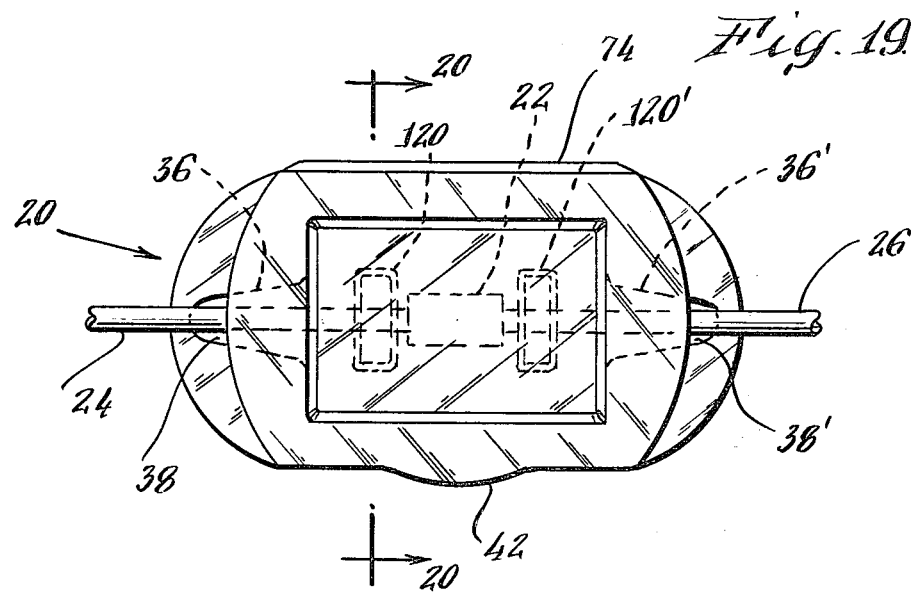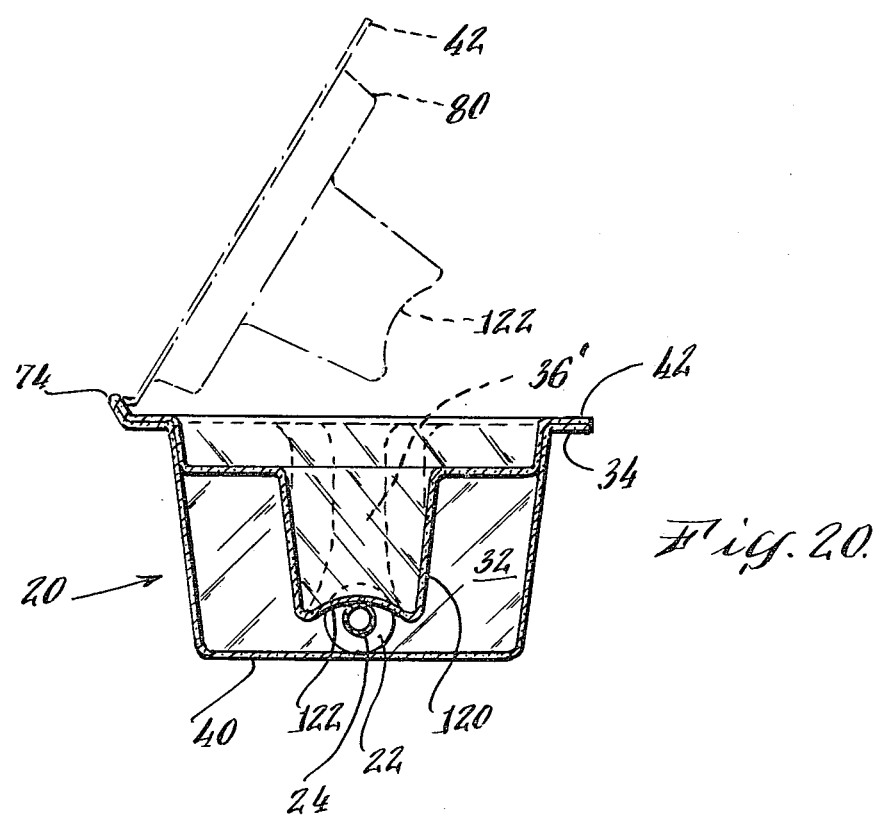

4,353,367

CONTAINER FOR STERILIZING A FLEXIBLE TUBE

FIELD OF THE INVENTION

This invention relates to the medicinal field of liquid treatment of flexible tubes generally used with patients and, in particular, to a device for in situ sterilization of a catheter which is in communication with the peritoneum membrane region of a patient.

BACKGROUND OF THE INVENTION

In the field of blood dialysis, several procedures are used, one of which employs a kidney machine. In another technique, known as peritoneal dialysis, the patient's peritoneum membrane is used. As part of this peritoneal dialysis, an infusion of a cleansing solution occurs through a dialysis catheter which is permanently embedded and which liquid is subsequently drained. In this procedure, the external end of the catheter is initially opened for connection to a dialysate tubing through which the solution is infused to the peritoneum cavity. After a suitable time, the junction between the catheter and dialysate tubing is broken so that the infused liquid inside of the patient's body can be drained. It is imperative that the entire peritoneal dialysis procedure be done while preserving the sterility of the various devices used. Hence, initial opening of the peritoneal dialysis catheter and the subsequent breaking of the junction with the dialysate tubing must be carried out in a sterile manner. Sterilization is normally done by employing a disposable cup containing a sterilizing liquid such as povidoneiodine and submerging the peritoneal dialysis catheter end and dialysate tubing junction in the solution for a five to ten minute soak before the junction is opened.

Since the peritoneum membrane is susceptible to infection, great care is exercised to assure that the peritoneal catheter junction is properly submerged in the sterilizing liquid and for the proper time. In practice this means that either the patient holds the cup and catheter with a sterile glove under supervision by a nurse who also is doing other steps in the peritoneal dialysis procedure or the nurse holds the cup and catheter for the required soaking time. The technique of cup soaking of the catheter junction is awkward, requires a substantial amount of sterilizing liquid, is not sufficiently free of risk of infection, and tends to spill sterilizing liquid on the patient.

Devices for sterilizing catheters, needles and other tools used in medical procedures, of course, are well known in the art. For example, in U.S. Pat. No. 3,488,141 to Rausing, a technique and mechanism is described for sterilizing the internal lumen of a plastic tube as well as its external surface. This involves injecting a sterilizing liquid inside a portion of the tube and placing this portion between pressure rollers mounted inside a container in which a sterilizing liquid is placed. In the U.S. Pat. No. 1,343,779 to Herbert, a sterilizing pan is shown with a cover having a slotted opening on one side to receive an electric wire for a heater to be placed on the bottom of the heater. A cold sterilizer is shown in U.S. Pat. No. 4,141,956 wherein a tray is hinged to a lid for submersion under a sterilizer liquid when the lid is closed. These prior art sterilizing devices are, however, not particularly useful for in situ catheter sterilization in a peritoneal dialysis procedure.

SUMMARY OF THE INVENTION

With a disposable device for the liquid treatment of a flexible tube in accordance with the invention such as sterilizing of a portion of a catheter, a peritoneal dialysis procedure may be carried out with greater ease, less spillage and more convenience to a patient while freeing a nurse from having to hold the container used for soaking or stand in attendance during the soaking period.

This is accomplished by employing, as described herein with reference to one embodiment, a lightweight disposable container having a basin which is sized to retain a limited amount of sterilizing liquid to a depth sufficient to submerge the external end of the embedded peritoneal catheter or the junction between the catheter and a dialysate tubing. The container is further provided with at least one integrally molded projection to clamp the catheter and thus maintain the catheter end submerged in the sterilizing liquid near the bottom of the basin.

The container is shaped so as to be conveniently positioned in a stable manner on the patient while the end of the dialysis catheter is held submerged in the container basin. As described herein with reference to one embodiment, the basin has a flat bottom with sufficient surface area to maintain an upright position during use without having to hold the container.

Submergence in the container basin of the end of the dialysis catheter is maintained as described in reference to several embodiments in accordance with the invention with an integrally molded projection or a plurality of them extending from a lid, a basin side wall or bottom wall. In one form of the invention, a projection extends towards a wall or another projection, leaving a gap sized to releasably grip the catheter to place its end in the vicinity of the basin bottom. This enables a convenient insertion of the dialysis catheter and dialysate tubing junction in the basin and easy release after soaking without physical contact of the sterilized end or junction.

As described herein with reference to one device in accordance with the invention, for sterilizing the dialysis catheter, the side wall of the basin is provided with a pair of oppositely spaced inlets. The inlets are shaped at an incline towards the basin bottom to laterally confine and vertically supportively guide the dialysis catheter and dialysate tubing towards the basin bottom. The inlets are more narrow in cross section than the basin, thus advantageously reducing the sterilizing liquid content of the container needed to submerge the catheter end or junction with other tubing. The inlets further serve to reduce the curvature of the catheter and tubing as they slope into the container from an upper surface. This reduces a tendency to lift out of the basin due to a natural resiliency of the catheter or tubing.

An advantageous reduction of spillage of sterilizing liquid is obtained by employing projections in the inlets, thus providing a gap for frictionally engaging the catheter and tubing while also restricting a passageway through which liquid has difficulty to escape and thus spill. The inclusion of an integrally molded hinged lid to overlie the basin and at least part of the inlets result in a practically spill-proof device for sterilized soaking of the catheter end.

It is, therefore, an object of the invention to provide a lightweight disposable device for the liquid treatment of a flexible tube such as the sterilization of a portion of a catheter, in a convenient but sterile manner requiring a small amount of liquid while retaining the flexible tube without having to hold the container.

This and other objects and advantages of the invention can be understood from the following detailed description of several embodiments described in conjunction with the drawings.

BRIEF DESCRIPTION OF DRAWINGS

FIG. 3 is a perspective view of the sterilizing container of FIG. 1;

FIG. 4 is a top plan view of the sterilizing container of FIG. 3 but with the lid closed;

FIG. 5 is a partial section view taken along the lines 5—5 in the view of the sterilizing container as shown in FIG. 4;

FIG. 6 is a section view of an inlet taken along lines 6—6 in FIG. 5;

FIG. 7 is a side view in elevation of the sterilizing container as shown in FIG. 4;

FIG. 8 is an enlarged section view taken along lines 8—8 in FIG. 4;

FIG. 9 is a side section view of the sterilizing container as shown in FIG. 3;

FIG. 10 is a bottom view of the sterilizing container as shown in FIG. 4;

FIG. 11 is a top plan view, partially broken away, of another form for a sterilizing container in accordance with the invention;

FIG. 12 is a section view taken along the lines 12—12 in FIG. 11;

FIG. 13 is a top plan view, partially broken away, of another embodiment for a sterilizing container in accordance with the invention;

FIG. 14 is a section view taken along the lines 14—14 in FIG. 13;

FIG. 15 is a top plan view of a modified form for a sterilizing container in accordance with the invention;

FIG. 16 is an enlarged section view taken along the lines 1-16 in FIG. 15;

FIG. 17 is a side view in elevation of the sterilizing container as shown in FIG. 15;

FIG. 18 is an enlarged section view taken along the lines 18—18 in FIG. 17;

FIG. 19 is a plan view of another form for a sterilizing container in accordance with the invention; and FIG. 20 is a section view taken along the lines 20—20 in FIG. 19.

DETAILED DESCRIPTION OF DRAWINGS

Figure 1:
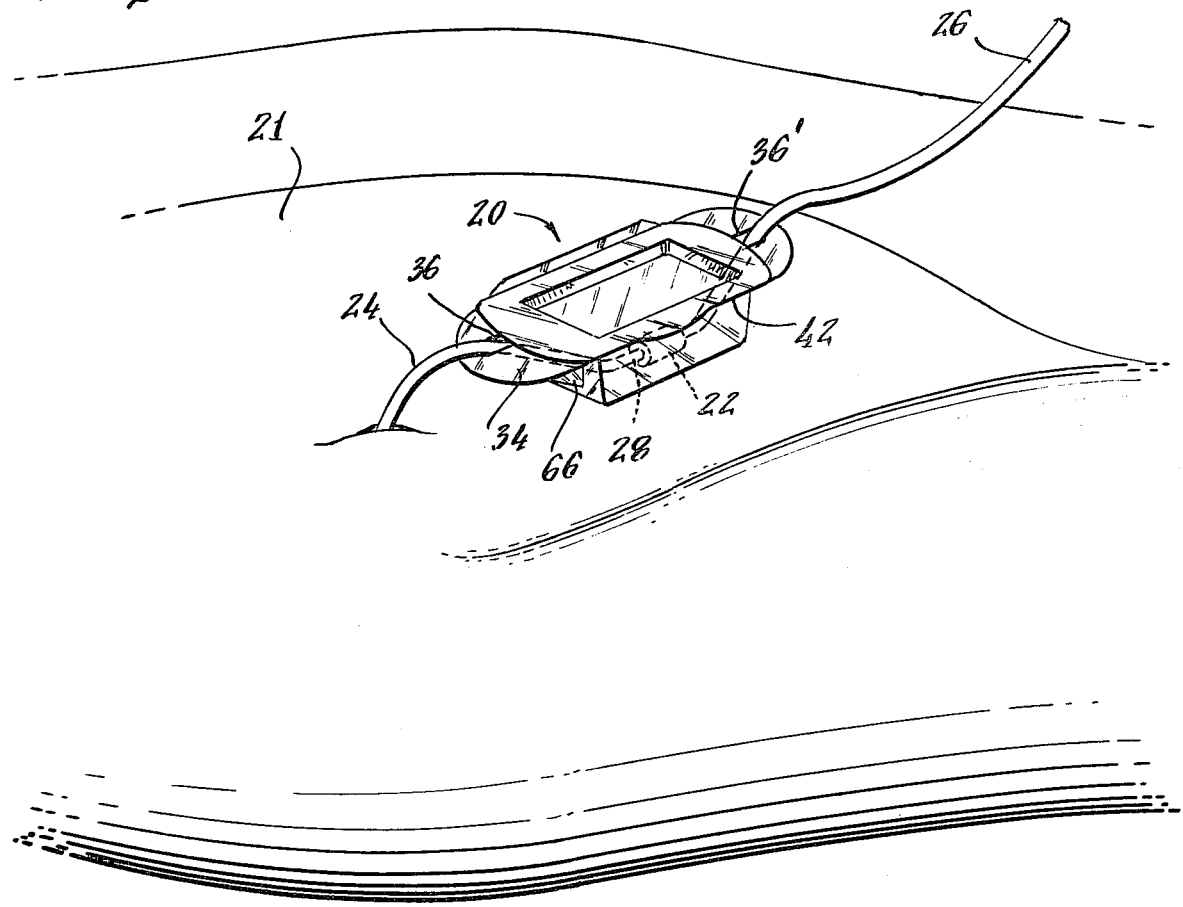
FIG. 1 is a perspective view of a container in accordance with the invention for in situ sterilizing of a peritoneal catheter end.
Figure 2:
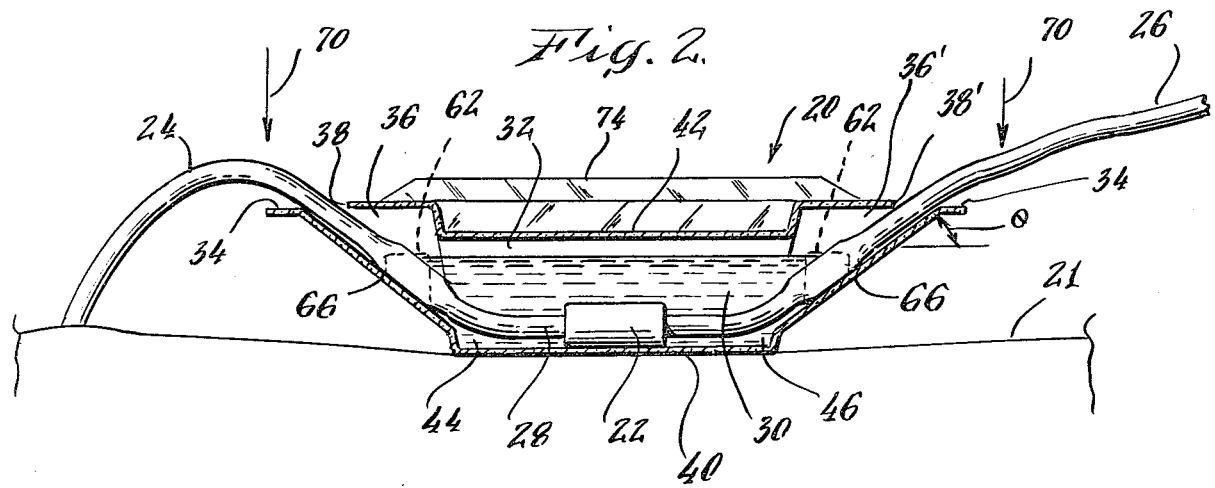
FIG. 2 is a side section view of the sterilizing container as shown in FIG. 1.

With reference to FIGS. 1 and 2, a container 20 is shown placed on a patient's abdomen 21 for sterilizing the junction 22 between a peritoneal dialysis catheter 24 and dialysate tubing 26. The dialysis catheter 24 is permanently embedded in an abdomen cavity bounded by the peritoneum membrane. The dialysate tubing 26 is connected to catheter 24 to initially infuse a solution from a source (not shown) into the peritoneum bounded cavity. The solution acts to cleanse the blood in the blood rich peritoneum membrane and requires to be drained after the procedure. Following the cleansing and draining procedure, the connection between the dialysis catheter end 28 and tubing 26 at junction 22 is broken and a sterile plug (not shown) inserted in catheter end 28.

The peritoneum membrane area is extremely vulnerable to infection and for that reason great care must be exercised to avoid physical contact or contamination with any catheter surfaces that lead to the peritoneum membrane. This means that before the catheter plug is removed for connection to tubing 26 and after the above described procedure has been completed and the connection at junction 22 needs to be broken so that the patient may resume normal activities, the catheter end 28 and junction 22 must be properly sterilized by soaking in an appropriate solution 30 such as povidone iodine.

Container 20 is particularly useful for sterilizing of catheter end 28 or junction 22 by providing a device which, as shown in FIG. 1, can be stably positioned on a patient's abdomen 21. Container 20 is formed of a lightweight plastic molded material, such as transparent polyethylene which can be vacuum formed over a suitable mold in accordance with well known vacuum forming techniques. The transparency enables a nurse to monitor proper submergence of junction 22 in solution 30.

Sterilizing container 20 is formed of a fully integrally molded body having a basin 32 extending below a generally flat upper surface 34. The catheter 24 and tubing 26 are placed into basin 32 through basin inlets 36—36' respectively and which intersect the upper surface 34 at openings 38—38' and extend towards the bottom 40 of basin 32 along an incline to gradually curve a flexible tube into the basin 32. A lid 42 which is an integrally molded part of container 20 is joined to upper surface 34 to overlie and cover the otherwise open basin 32 and at least partially close off inlet openings 38—38' to thus reduce a tendency to spill sterilizing solution 30. The angle of inclination for inlets 36—36' may vary, though for the embodiment shown an angle $\theta$ of the order of about 30° relative to upper surface 34 was found satisfactory.

With a sterilizing container, such as 20, and in accordance with the invention the dialysis catheter 24 and dialysate tubing 26 can be gently curved at 44 and 46 to lie submerged under solution 30 in the vicinity of the basin bottom 40 despite the tendency of the catheter or tubing to pop up to the surface of solution 30 due to buoyancy or resiliency. Retention is obtained as more clearly shown in FIGS. 3–10 with integrally molded projections such as 48—48', and 50—50' formed in a peripheral side wall 52 of basin 32. Side wall 52 is generally rectangularly contoured except where side wall 52 forms inlets 36—36'.

Projections such as 48 and 50 are located to lie along inlets 36—36' respectively. The projections 48—48', 50—50' extend from lateral walls 51—51' of inlets 36—36' and are oppositely located from each other towards the lower ends 54—54' of inlets 36—36' and are sized to define gaps, such as 56, 58 between them. The widths of gaps 56, 58 are selected so that catheter 24 and dialysate tubing 26 can be pushed into a gap with sufficient interference to enable projections 48—48' and 50—50' to frictionally clamp and thus retain them.

The sizes of projections 48 and 50 are selected commensurate with the desired sizes of the gaps 56, 58. When the diameters of catheter 24 and tubing 26 are the same, gaps 56, 58 are made the same and the projections 48, 50 are made of equal size as shown in FIGS. 3–10.

Differently sized flexible tubing can be accommodated by sizing the gaps between projections correspondingly.

The projections 48, 50 are preferably formed, insofar as the vacuum molding process so permits, with a slight widening at the bottom of the gaps 56, 58 such as at 60 in FIG. 9. In this manner insertion of flexible tubing such as dialysis catheter 24 or dialysate catheter 26 into a gap 56 or 58 is accompanied with enhanced retention strength, while still allowing easy removal.

In the embodiment of FIGS. 1-10, the projections 48, 50 are generally shaped, as more clearly shown in FIG. 9, in the form of portions of cylinders with flat partially circular tops 62 and generally straight but slightly inclined sides 63 so as to widen the gaps below tops 62.

In FIGS. 3-10, the basin inlets 36—36' are formed to commence at openings 38, 38' in upper surface 34 and extend downwardly at an angle towards the basin bottom 40. The size of the cross section of each inlet 36 is so selected that lateral inlet side walls 51—51' freely receive either catheter 24 or dialysate tubing 26, but also laterally confine them in cooperation with a smoothly merging, upwardly supporting inlet wall 66.

Wall 66 as illustrated in FIGS. 6 and 10 has, towards the upper end 64, a generally cylindrical cross section sized to closely support a tubing while smoothly merging with side walls 51—51'. Below projections 48 or 50 near bottom 40, wall 66 widens and has a flatter shape.

Inlets 36—36' form longitudinal extensions for basin 32, but with reduced cross section so that most of the sterilizing liquid is in a main central part. The projections 48, 50 serve to restrict the inlets 36—36' and thus lessen spillage of sterilizing liquid back through inlets 36—36'.

The frictional retention of tubing such as catheter 24 or tubing 26 by projections 48, 50 is particularly advantageous for maintaining junction 22 (see FIG. 2) submerged under solution 30 near the bottom 40. Without projections such as 48 or 50 tubing fed into basin 32 would tend to lift out of the liquid 30 due to buoyancy or as a result of an upward pivot action from the external portions of catheter 24 and tubing 26 whose weight cause a downward force at about as indicated by arrows 70 in FIG. 2.

Lid 42 is an integrally molded part of container 20 and is connected along a normally biased open hinge segment 74 formed by thermo pressing of a pair of edges 76, 78 (see FIG. 9) closely together. The lid 42 has an indentation 80 sized and shaped to snugly fit inside the upper opening 82 of basin 32. Interfering tabs 84, 86 (see FIG. 8) are respectively employed on the external side 88 of indentation 80 and opposite thereto on the upper edge of peripheral side wall 52 at opening 82. The tabs 84, 86 are sized to slightly interfere with each other and thus provide upon closure of lid 42 a latching action by deformation of local walls sufficient to maintain the lid 42 closed against the normally biased open hinged lid 42 and such pull that may be normally expected on lid 42 by catheter 24 or dialysate tubing 26. The latching action is sufficiently weak, however, to facilitate opening of lid 42 without excessive jarring motion.

Lid 42 is further provided with flat segments 90—90' sized to partially overlie openings 38—38' when closed as illustrated in FIG. 4. Upper surface 34 is recessed at 92 to provide a convenient hold on lid 42.

The container 20 is further sized to contain a limited amount of sterilizing liquid in basin 32. The latter is, therefore, sized and shaped to contain sufficient liquid to submerge a catheter end 28, or junction 22 (see FIGS. 1 and 2) in a size enabling stable positioning of container 20 on a patient, yet without requiring an excessive amount of sterilizing liquid. In one embodiment, basin 32, without including the inlets 36—36' had a rectangular shape with, as illustrated, a flat bottom 40 with dimensions of about 6 cm long, 4 cm wide and two and a half cm deep for a total volume of about 60 ml. In such container, approximately 30 ml of sterilizing liquid 30 was usually needed to sterilize a junction 22 between a dialysis catheter 24 and dialysate tubing 28. The basin size may be made larger, but generally a basin 32 having a total volume of less than about 120 $cm^3$ (120 ml capacity) is preferred. If the container 20 and thus basin 32 were made large, an increasing amount of material to make containers 20 would be needed, thus increasing its cost, detracting from its disposability, while also tending to require more sterilizing liquid 30. When the container 20 is made too small, however, it tends to rest less stably on a patient and the basin 32 may not always properly submerge a catheter end 28 or junction 22. The container is of light weight construction, of the order of about 0.3 oz.

Variations from the described embodiment of FIGS. 1-10 can be made. For example, as shown in FIGS. 11 and 12, a lightweight disposable container 20 is shown made in a similar manner as described with reference to FIGS. 1-10 of a thin walled, approximately one mm thick, transparent vacuum molded plastic. The retention of a flexible tubing to be submerged in basin 32 of the container 20 is obtained by employing a single projection 102 in each inlet 36—36'. Each projection 102 is sized to approach an opposite inlet side wall 51 while leaving a gap 104 sized to receive and at least partially pass for frictional clamping a flexible, pinchable tube such as catheter 24 or dialysate tubing 28.

In some instances it may be desirable to retain a tubing only at one end. For example, if only the dialysis tubing end 28 as shown in FIG. 2 would need to be sterilized, a container having a single inlet 36 with a single projection 102 could be used to submerge end 28 under sterilizing liquid 32. One might also have another inlet 36' without a projection.

In the embodiment illustrated in FIGS. 13 and 14, a plurality of semicylindrical cross section projections 106 are shown integrally molded to bottom wall 31 of a container 20. The projections are spaced from each other to form gaps 108, 110 sized to frictionally receive and retain a tubing and are aligned respectively with inlets 36-36'.

In FIGS. 15-18, a container 20 is shown with inlets 36-36' as in the embodiment illustrated in FIGS. 1-10. Projections 112, however, are shown extending from side walls 51-51' at a higher location of inlets 36-36' with the tops 62 of projections 112 flush with upper surface 34. The indentation 80 of lid 42 is provided with a single enlarged tab 84' centrally located of edge 88 opposite a tab 86' on the upper rim of the basin's peripheral side wall 52.

With reference to FIGS. 19 and 20, a container 20 is shown wherein projections 120-120' are shown extending from the indentation 80 of lid 42. When lid 42 is closed, projections 120-120' extend into basin 32 to a depth sufficient to engage and thus maintain submergence of a flexible tubing such as catheter 24 or dialysate tubing 28. Although a pair of projections 120 are illustrated, a single one could be employed.

Each projection 120 is vacuum formed with lid 42 and has at its end a recess 122 so as to more easily capture and retain a tubing as illustrated. The projections 120 are hollow and tapered towards the basin bottom 40 and are aligned with inlets 36–36' when lid 42 is closed.

Having thus described several embodiments for sterilizing tubes such as a peritoneal dialysis catheter and the like, the advantages of the invention can be appreciated. A convenient to use, disposable container of lightweight material is provided for in situ sterilizing of a permanently embedded peritoneal catheter. Variations from the described embodiments can be made without departing from the scope of the invention.

What is claimed is:

1. A disposable device for liquid treatment in a medical procedure of a portion of a flexible tube comprising
    a lightweight self-supporting disposable plastic molded container having a liquid retaining basin formed by a peripheral wall and a bottom wall, said container having an upper surface which intersects the peripheral wall to form an upper opening for the basin, through which opening the portion of the flexible tube is received, said basin, being sized to retain a limited amount of liquid to a depth sufficient to submerge a portion of the flexible tube to be treated;
    said container being further provided with at least one projection which is attached to the container and is sized and located to releasably maintain, in cooperation with a wall of the container, said tube portion in the vicinity of the bottom wall of the basin.

2. A disposable device for liquid treatment in a medical procedure of a portion of a tube as set forth in claim 1 wherein the at least one projection is located a predetermined distance from the peripheral wall to enable frictional gripping of the tube between the peripheral wall and the projection.

3. A disposable device for liquid treatment in a medical procedure of a portion of a flexible tube as set forth in claim 1, wherein said container is provided with first and second projections which are oppositely spaced with respect to each other with a gap between the projections being sized to receive with interference and frictionally retain the tube between the projections.

4. A disposable device for liquid treatment in a medical procedure of a portion of a flexible tube as set forth in claim 1 wherein said container is formed of a transparent plastic molded material.

5. A disposable device for liquid treatment in a medical procedure of a portion of a flexible tube as set forth in claim 1 wherein said container is provided with an integrally molded cover hinged to the upper surface and sized to overlie said upper opening of the basin to retain liquid therein.

6. A disposable device for liquid treatment in a medical procedure of a portion of a flexible tube as set forth in claim 5 wherein said cover is provided with an indentation shaped to project into the basin when the cover is closed, and means attached to the cover indentation and the peripheral wall to releasably retain the cover in its closed position.

7. A disposable device for liquid treatment in a medical procedure of a portion of a flexible tube as set forth in claim 1, 3, 4 or 5 wherein said peripheral wall is further shaped to form an inlet for the tube, said inlet extending from the vicinity of the basin bottom to said upper surface.

8. A disposable device for liquid treatment in a medical procedure of a portion of a flexible tube as set forth in claim 1, 2, 4 or 5 wherein said peripheral wall is further shaped to form an inlet for the tube, said inlet extending from the vicinity of the basin bottom to said upper surface, and wherein said projection is formed by the peripheral wall in the inlet.

9. A disposable device for liquid treatment in a medical procedure of a portion of a flexible tube as set forth in claim 1, 3, 4 or 5 wherein said peripheral wall is further shaped to form first and second inlets, each of said inlets extending upwardly from the vicinity of the basin bottom to said upper surface, and wherein the peripheral wall in each of said inlets is shaped to form a pair of opposing projections which are spaced from each other across a gap to frictionally receive and retain a tube.

10. A disposable device for liquid treatment in a medical procedure of a portion of a flexible tube as set forth in claim 1, 2, 3, 4 or 5 wherein said container peripheral wall is further shaped to form an inlet for the catheter, said inlet extending from inside the basin at an inclined angle to the upper surface, said inlet being shaped to laterally confine and upwardly support the tube, the cross section of said inlet being substantially smaller than the cross section of the basin.

11. A disposable device for liquid treatment in a medical procedure of a portion of a flexible tube as set forth in claim 10 wherein said projection is located in the inlet to retain said tube and constrict the inlet to inhibit escape of liquid through said inlet.

12. A disposable device for sterilizing a portion of a catheter comprising
    a lightweight disposable plastic molded container having a liquid retaining basin formed by a peripheral side wall and a bottom wall, said container having an upper surface which intersects the peripheral side wall to form an upper opening for the basin, said basin having a sufficient depth to submerge the portion of the catheter;
    said peripheral side wall being shaped to form at least one catheter inlet of smaller cross section than said basin and extending from the upper surface to the vicinity of the basin bottom wall along an incline enabling a gradual curving of the catheter into the basin, said inlet having a cross section sized to snugly receive said catheter and obstruct spillage of liquid from the basin through said inlet; and
    means attached to the container for releasably clamping said catheter to maintain said catheter portion in the vicinity of the basin bottom.

13. A disposable device for sterilizing a portion of a catheter as claimed in claim 12 wherein said means comprises:
    a least one projection which is integrally molded to the container and is sized and located to releasably grip said catheter.

14. A disposable device for sterilizing a portion of a catheter as claimed in claim 13 wherein said projection is located in said inlet and extends towards a side wall thereof with a spacing selected to receive said catheter with interference.

15. A disposable device for sterilizing a portion of a catheter as claimed in claim 12 wherein said means further comprises a pair of projections which are integrally molded parts of the container, said projections being oppositely spaced from each other with a gap between them sized to frictionally and releasably receive said catheter, with the projections located to place said catheter portion in the vicinity of the basin wall.

16. A disposable device for sterilizing a portion of a catheter as claimed in claims 12, 13, 14 or 15 and further including a lid sized to overlie the upper opening of the basin and partially cover said inlet at the upper surface, said lid being integrally hingedly connected to said upper surface.

17. A disposable device for sterilizing the exposed end of a flexible peritoneal catheter tube in communication with the peritoneum of a patient's body comprising a lightweight disposable plastic molded container having an upper surface and an upwardly open basin extending below the upper surface, said basin being sized to retain a limited amount of sterilizing liquid to a depth sufficient to submerge the end of the catheter tube when said limited amount of sterilizing liquid is placed within the basin, said basin having a generally level bottom of sufficient area to position the container in a stable manner on the patient while said catheter tube end is placed inside the basin;

said basin further having a peripheral side wall which extends to the upper surface to form an upper opening for the basin, said peripheral wall being formed with first and second outwardly extending catheter tube inlets, said inlets commencing at the upper surface and terminating near the bottom of the basin, said inlets being sized and shaped to laterally confine and upwardly support a catheter tube placed through an inlet into the basin;

said peripheral wall further being provided at said inlets with means for releasably retaining the end of the catheter tube in the vicinity of the basin bottom for submersion of the catheter tube in a sterilizing liquid is placed inside the basin.

18. A disposable device as set forth in claim 17 wherein said means further comprises at each inlet a pair of oppositely spaced peripheral wall projections which laterally extend into the inlet towards each other to form a gap between the projections, said gap being upwardly open to receive a catheter tube and further being sized smaller than the cross section of the catheter tube for its frictional retention between the oppositely spaced projections when the catheter tube is placed inside the basin.

19. A disposable device as set forth in claim 17 or 18 wherein said container is further provided with a cover hinged to the upper surface, said cover having an indentation which is shaped to frictionally fit with the peripheral wall and inside said upper opening, said cover further partially extending over the inlets at said upper surface.

20. A disposable device as set forth in claim 19 wherein the indentation of the cover and an upper portion of the peripheral wall are provided with tabs oppositely located to lockingly interfere with each other and retain the cover in a basin covering position for retention of liquid located in the basin.

21. A disposable device as set forth in claims 17 or 18 wherein said inlets are inclined to extend upwardly from the vicinity of the basin bottom to the upper surface, said inlet inclination being selected to reduce bending of the catheter tube when placed in the basin for submersion without appreciably affecting the positional stability of the container when placed on a patient.

22. A disposable device as set forth in claim 17 or 18 wherein said container is formed of a transparent plastic material to enable external monitoring of the submersion of the catheter tube in the sterilizing liquid.

23. A disposable device as set forth in claim 17 or 18 wherein said basin has a liquid holding capacity of the order of about generally less than about 120 ml.

* * * * *